United States Patent [19]

Makino et al.

[11] Patent Number: 4,665,212

[45] Date of Patent: May 12, 1987

[54] PROCESS FOR PREPARING 2-(4-HYDROXYPHENOXY) ALKANOIC ACID COMPOUNDS

[75] Inventors: Kenzi Makino, Shiki; Shigeaki Akiyama; Kenzow Fukuda, both of Narashino; Gozyo Sakata, Kokubunji, all of Japan

[73] Assignee: Nissan Chemical Industries Ltd., Tokyo, Japan

[21] Appl. No.: 788,890

[22] Filed: Oct. 18, 1985

[30] Foreign Application Priority Data

Oct. 31, 1984 [JP] Japan ................. 59-230873

[51] Int. Cl.⁴ ............................................. C07C 69/76
[52] U.S. Cl. ........................................ 560/61; 562/471
[58] Field of Search .......................... 560/61; 562/471

[56] References Cited

U.S. PATENT DOCUMENTS 3,198,823 8/1965 Akabayashi et al. ............... 260/458
4,489,207 12/1984 Becker et al. ......................... 560/61
4,532,346 7/1985 Rehn et al. ............................ 560/61

FOREIGN PATENT DOCUMENTS

82/00639 3/1982 PCT Int'l Appl. ................... 560/61

*Primary Examiner*—Paul J. Killos
*Attorney, Agent, or Firm*—Oblon, Fisher, Spivak, McClelland & Maier

[57] ABSTRACT

A process for preparing a 2-(4-hydroxyphenoxy) alkanoic acid, its ester or alkali metal salt, or an optical isomer thereof, which comprises condensing hydroquinone or an alkali metal salt of hydroquinone with a compound having the formula:

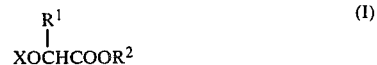

wherein X is a p-toluenesulfonyl group, a methanesulfonyl group, a benzylsulfonyl group, a p-chlorobenzenesulfonyl group or a benzenesulfonyl group, $R^1$ is a hydrogen atom or a lower alkyl group, and $R^2$ is a hydrogen atom, an alkyl group or an alkali metal cation, or its optical isomer in the presence of a base.

12 Claims, No Drawings

PROCESS FOR PREPARING 2-(4-HYDROXYPHENOXY) ALKANOIC ACID COMPOUNDS

The present invention relates to a process for producing 2-(4-hydroxyphenoxy)alkanoic acid compounds or their optical isomers. More particularly, the present invention relates to a process for preparing 2-(4-hydroxyphenoxy)alkanoic acids, their esters or alkali metal salts, or optical isomers thereof.

2-(4-Hydroxyphenoxy)propionic acid is disclosed in Japanese Unexamined Patent Publication No. 16475/1981 (or UK Patent Publication GB2042539B), Japanese Unexamined Patent Publication No. 22371/1979 or Japanese Unexamined Patent Publication No. 40767/1978, and it is a compound useful as an intermediate for excellent herbicides. More importantly, the herbicides prepared from 2-(4-hydroxyphenoxy)propionic acid as the intermediate, have an asymmetric carbon atom in their structures, and therefore they have two optical isomers. One of the isomers, i.e. the D-form isomer, is known to have a strong herbicidal activity (see e.g. Japanese Unexamined Patent Publication No. 55372/1981). Accordingly, if a herbicide is prepared by using only the optical isomer having the strong herbicidal activity, the necessary dose may be substantially a half as compared with the dose of the racemic modification, which is significant not only from the viewpoints of the environmental protection and conservation of resources, but also from the viewpoint of the industrial advantage that the costs for the production or the application of the herbicide can be reduced.

As a conventional method for the production of optically active 2-(4-hydroxyphenoxy)propionic acid compounds, there is a process disclosed in Japanese Unexamined Patent Publication No. 95237/1984 (hereinafter referred to as "conventional process A"), wherein an optically active 2-halopropionic acid and hydroquinone are condensed in an aqueous alkaline solution. On the other hand, as a conventional method for the production of esters of optically active 2-(4-hydroxyphenoxy)propionic acid, there is a process disclosed in published West German Patent Application No. G.O.DE3150233 (hereinafter referred to as "conventional process B"), wherein an optically active 2-halopropionic acid ester and hydroquinone are condensed in the presence of both a DMSO solvent and calcium hydroxide.

In the above-mentioned patent publication relating to the conventional process A, there is no substantial specific description as to the process and the physical properties of the optically active 2-(4-hydroxyphenoxy) propionic acid, and therefore the results are not known.

In the conventional process B, an expensive optically active material such as optically active n-butyl 2-chloropropionate is used, and nevertheless, it is difficult to avoid partial racemization during the reaction, whereby it is impossible to obtain an optically highly pure alkyl ester of 2-(4-hydroxyphenoxy)propionic acid. (Example 3 of G.O.DE3150233 discloses the production of optically active n-butyl 2-(4-hydroxyphenoxy)propionate, wherein the angle of rotation is disclosed to be $[\alpha]_D^{25} +11.8°$, which clearly indicates racemization having taken place, as compared with the value $[\alpha]_D^{25} +57.6°$ (neat) of optically active n-butyl 2-(4-hydroxyphenoxy)propionate prepared by the present inventors.

As a problem common to the conventional processes A and B, there is a drawback that both of the two hydroxyl groups of hydroquinone are likely to be alkylated to form a by-product in a substantial amount, whereby the yield of the desired product is reduced and the expensive optically active material is thereby unnecessarily wasted.

Namely, from the technical point of view, it has been desired firstly to produce an optically highly pure 2-(4-hydroxyphenoxy)propionic acid, and secondly to obtain the mono-substituted product of hydroquinone in good selectivity. It has been required to solve such two problems in order to make the processes industrially applicable.

The present inventors have conducted extensive researches to develop an industrial process for the production of an optically active 2-(4-hydroxyphenoxy) alkanoic acid, and have finally established a process whereby an optically highly pure 2-(4-hydroxyphenoxy) alkanoic acid or its ester or alkali metal salt is obtainable in high selectivity efficiently without using a special apparatus.

Namely, the present invention provides a process for preparing a 2-(4-hydroxyphenoxy)alkanoic acid, its ester or alkali metal salt, or an optical isomer thereof, which comprises condensing hydroquinone or an alkali metal salt of hydroquinone with a compound having the formula:

wherein X is a p-toluenesulfonyl group, a methanesulfonyl group, a benzylsulfonyl group, a p-chlorobenzenesulfonyl group or a benzenesulfonyl group, $R^1$ is a hydrogen atom or a lower alkyl group, and $R^2$ is a hydrogen atom, an alkyl group or an alkali metal cation, or its optical isomer in the presence of a base.

Now, the present invention will be described in detail with reference to the preferred embodiments.

The present invention is concerned with a process for preparing a 2-(4-hydroxyphenoxy)alkanoic acid or its ester or alkali metal salt. For the preparation of the racemic modifications of these products, the process of the present invention can be conducted without paying any particular attention to the optical arrangement or racemization with respect to the starting materials or the manner for the preparation. A feature of the process over the conventional techniques is that an inexpensive material L(-)lactic acid is employed as a starting material for the product of the present invention.

Ethyl L(—)-2-(p-toluenesulfonyloxy)lactate (hereinafter referred to simply as "TLE"), ethyl L(—)-2-(p-chlorobenzenesulfonyloxy)lactate (hereinafter referred to simply as "CLE"), ethyl L(—)-2-(methanesulfonyloxy) lactate (hereinafter referred to simply as "MLE"), ethyl L(—)-2-(benzylsulfonyloxy)lactate (hereinafter referred to simply as "BzLE") and ethyl L(—)-2-(benzene sulfonyloxy)lactate (hereinafter referred to simply as "BLE") used in the present invention, were synthesized from ethyl L(—)-lactate and the corresponding sulfonylchloride derivatives, in accordance with the methods as disclosed by e.g. J. Kenyon (J. Chem. Soc., 1924, 399), J. H. H. Chan (J. Agric. Food. Chem., 23, 1008(1975)) and S. R. Mark (Ger. Offen., 2650434 (1977)). An alkali metal salt of hydroquinone, particularly the disodium salt, can be synthesized by a usual method by using metallic sodium in anhydrous ethanol, or by reacting a calculated amount of sodium hydroxide in a solvent for the reaction. In this case, the quality of the desired product is substantially affected depending on whether the reaction is conducted while removing the water formed as a by-product or the reaction is continued in the presence of such water.

Now, the features of the present invention will be described in detail with reference to the case where TLE is used. When reacted with equimolar sodium hydroxide at a low temperature (preferably not higher than 15° C.) in a reaction solvent such as ethanol or water, the ester group of TLE readily undergoes hydrolysis to form a sodium salt of the acid of TLE. This operation has an outstanding feature that no substantial racemization takes place. Then, when this reaction product is reacted with a reaction product obtained by reacting from 2 to 4 equivalents of sodium hydroxide with one equivalent of hydroquinone in an ethanol solution, Walden inversion condensation takes place preferentially, whereby a solution of a sodium salt of D-form 2-(4-hydroxyphenoxy) propionic acid is obtained. Then, this reaction system is acidified by an introduction of hydrogen chloride gas, and slowly heated, whereby esterification takes place to form a solution of the desired product i.e. ethyl D(+)-2-(4-hydroxyphenoxy)-propionate. From this solution, the desired product is isolated by a usual method, whereby TLE is obtainable in a yield of from 70 to 80% with an optical purity of from 90 to 95%. The reaction scheme 1 is shown below:

Reaction scheme 1

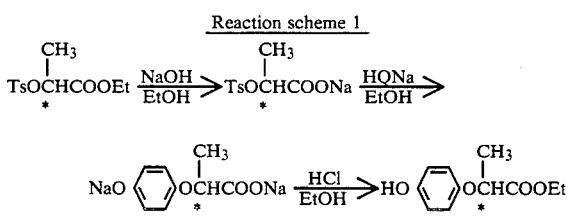

wherein Ts is a tosyl group, Et is an ethyl group, and HQNa is a disodium salt of hydroquinone.

If this reaction is conducted in an anhydrous solvent or by means of a disodium salt of hydroquinone, no hydrolysis of the ester takes place, but carbanions of TLE are likely to form, and consequently the degree of racemization increases, whereby the 2-(4-hydroxyphenoxy) propionate finally obtained will have a low optical purity. However, the diester product of hydroquinone formed as a by-product will be little, and therefore this method may be regarded as suitable for the synthesis of the racemic modification.

Further, this process has a feature that an ester other than the ethyl ester can be synthesized by selecting an optional alcohol as the reaction solvent or as an esterification agent at the esterification stage. Thus, one of the features of the reaction scheme 1 is that in order to obtain a desired compound with a high optical purity, TLE is firstly converted to a sodium salt of the acid of TLE in a water-containing solvent at a low temperature, and then condensed with hydroquinone or its sodium salt. The optical purity of the compound obtained by this process adequately satisfies the requirement as the starting material for the herbicides, and the by-product dialkyl ether of hydroquinone is as low as a few percent, which makes the process very economical.

In the reaction scheme 1, the alkali metal hydroxide may be, for instance, lithium hydroxide, sodium hydroxide or potassium hydroxide. From the economical point of view, sodium hydroxide is most preferred. TLE is used preferably in an equimolar amount or from 0.7 to 2.0 mols relative to one mol of hydroquinone. The sodium salt of the acid of TLE may be preliminarily formed in the reaction system, or the one separately synthesized outside the system may be supplied for the reaction. For the synthesis of the sodium salt of the acid of TLE, the reaction temperature may vary depending upon the type of the alkali metal and the type of the solvent, but is preferably within a range of from $-20°$ to $50°$ C. The reaction temperature is most preferably from $0°$ to $15°$ C. when the racemization is taken into account. The water-containing solvent should preferably be the same as the solvent for the subsequent condensation with hydroquinone or its sodium salt. However, good results can be obtained when water is used alone as the solvent. However, in such a case, it is necessary to remove water for the subsequent reaction, such being undesirable from the viewpoint of energy saving.

In the reaction scheme 1, racemization hardly takes place during the condensation of the sodium salt of TLE with hydroquinone or its sodium salt, and the reaction temperature may be raised to a suitable extent in connection with the reaction rate. For instance, in the case of ethanol, the reaction is conducted at a temperature of from $20°$ to $70°$ C. In this case, the freed sodium sulfonate derivative may be recycled by using a suitable method for the recovery.

In the reaction scheme 1, the final esterification reaction may be conducted by using not only hydrochloric acid but also sulfuric acid as the catalyst. The esterification is usually conducted from $0°$ to $150°$ C., preferably from $30°$ to $80°$ C. As the alcohol for this purpose, it is practical to use a lower alkyl alcohol such as methanol, ethanol or n-butanol. However, the alcohol is not restricted to these specific examples.

By the development of a process for producing an optically active 2-(4-hydroxyphenoxy)propionic acid or its ester in high selectivity and with a high optical purity by reacting an optically active 2-(sulfonyloxy) lactic acid ester derivative or an optically active 2-(sulfonyloxy)lactic acid alkali metal salt derivative with hydroquinone or its alkali salt, it has now become possible to produce an alkyl ester of a 2-(4-heteroalkyloxyphenoxy)propionic acid as an active ingredient of excellent herbicides, in an industrially advantageous manner.

Now, the present invention will be described in detail with reference to Examples and a Reference Example. However, it should be understood that the present invention is by no means restricted by these specific Examples.

EXAMPLE 1

4.4 g of hydroquinone and 67.5 ml of ethanol were charged in a reactor, and after flushing with nitrogen, 6.4 g of sodium hydroxide was added thereto. The mixture was stirred for 1 hour, and then cooled to 10° C., and then 10.9 g of ethyl L(−)-2-(p-toluenesulfonyloxy)-lactate [[α]$_D^{20}$−35.7° CHCl$_3$; C=1.55%] was dropwise added. The mixture was stirred for 1 hour. Then, at the reaction temperature of 30° C., the mixture was stirred for further 2 hours. The reaction product thereby obtained was cooled to 10° C. and hydrogen chloride gas was introduced to acidify the reaction system. Then, ethanol was distilled off under atmospheric pressure. 10 ml of ethanol and 50 ml of benzene were added, and the solvent was again distilled off under atmospheric pressure. To the residue, 50 ml of water was added and extracted with benzene. The benzene layer was washed with a 5% sodium hydrogen carbonate solution and then with water, and dried, and then benzene was distilled off. The residue was purified by a silica gel column chromatography by using chloroform, whereby 6.7 g of the desired substance ethyl D(+)-2-(4-hydroxyphenoxy)propionate was obtained as a colorless liquid.

$[\alpha]_D^{25} + 41.7°$ CHCl$_3$; C=1.35%, e.e. 91%

EXAMPLE 2

4.4 g of hydroquinone and 67.5 ml of ethanol were charged into a reactor, and after flushing with nitrogen, 6.4 g of sodium hydroxide was added thereto. The mixture was stirred for 1 hour, and then cooled to 10° C., and 10.9 g of ethyl L(−)-2-(p-toluenesulfonyloxy)lactate $[[\alpha]_D^{20} - 35.7°$ CHCl$_3$; C=1.55%] was dropwise added. The mixture was stirred for 30 minutes. Then, at the reaction temperature of 60° C., the mixture was stirred for further 2 hours. To the reaction product thereby obtained, hydrogen chloride gas was introduced at 50° C. to acidify the reaction system, and the mixture was stirred for 15 minutes. Ethanol was distilled off under atmospheric pressure. After adding 50 ml of water thereto, the mixture was extracted with benzene. The benzene layer was washed with a 5% sodium hydrogen carbonate solution and then with water, and dried, and the benzene was distilled off. The residue was purified by a silica gel column chromatography using chloroform, whereby 6.4 g of the desired substance ethyl D(+)-2-(4-hydroxyphenoxy)propionate was obtained as a colorless liquid.

$[\alpha]_D^{25} + 41.5°$ CHCl$_3$; C=1.41%, e.e. 91%

EXAMPLE 3

4.4 g of hydroquinone and 67.5 ml of ethanol were charged into a reactor, and after flushing with nitrogen, 8.96 g of potassium hydroxide was added thereto. The mixture was stirred for 1 hour, and then cooled to 10° C., and 10.9 g of ethyl L(−)-2-(p-toluenesulfonyloxy)-lactate $[[\alpha]_D^{20} - 35.7°$ CHCl$_3$; C=1.55%] was dropwise added thereto. The mixture was stirred for 1 hour. Then, at the reaction temperature of 30° C., mixture was stirred for further 2 hours. While cooling the reaction product thereby obtained to a temperature of 10° C., hydrogen chloride gas was supplied to acidify the reaction system. Ethanol was distilled off under atmospheric pressure. 10 ml of ethanol and 50 ml of benzene were added, and the solvent was again distilled off under atmospheric pressure. To the residue, 50 ml of water was added, and the extraction was conducted with toluene. The toluene layer was washed with a 5% sodium hydrogen carbonate solution and then with water, and dried, and then toluene was distilled off. The residue was purified by silica gel column chromatography using chloroform, whereby 6.8 g of the desired substance ethyl D(+)-2-(4-hydroxyphenoxy) propionate was obtained as a colorless liquid.

$[\alpha]_D^{25} + 41.0°$ CHCl$_3$; C=1.40%, e.e. 90%

EXAMPLE 4

4.4 g of hydroquinone and 45 ml of ethanol were charged into a reactor, and after flushing with nitrogen, 4.8 g of sodium hydroxide was added thereto. The mixture was stirred for 1 hour. While cooling the mixture at 10° C., a sodium L(−)-2-(p-toluenesulfonyloxy)lactate solution [which was prepared by hydrolyzing 10.9 g of ethyl L(−)-2-(p-toluenesulfonyloxy)lactate $[[\alpha]_D^{20} - 35.7°$ CHCl$_3$; C=1.55%] in an equimolar sodium hydroxide solution, then distilling off the water under reduced pressure and adding 25 ml of ethanol] was dropwise added thereto, and the mixture was stirred for 1 hour. Then, at a reaction temperature of 50° C., the mixture was stirred for further 2 hours. While cooling the reaction product thereby obtained, at 10° C., hydrogen chloride gas was introduced to acidify the reaction system, and then ethanol was distilled off under atmospheric pressure. 20 ml of ethanol and 50 ml of benzene were added, and the solvent was again distilled off under atmospheric pressure. To the residue, 50 ml of water was added, and the mixture was extracted with toluene. The toluene layer was washed with a 5% sodium hydrogen carbonate solution and then with water, and dried, and then toluene was distilled off. The residue was purified by silica gel column chromatography using chloroform, whereby 6.2 g of the desired substance ethyl D(+)-2-(4-hydroxyphenoxy) propionate was obtained as a colorless liquid.

$[\alpha]_D^{25} + 38.0°$ CHCl$_3$; C=1.56%, e.e. 83%

EXAMPLE 5

1.6 g of sodium hydroxide and 35 ml of water were charged into a reactor. While stirring the mixture, 10.9 g of ethyl L(−)-2-(p-toluenesulfonyloxy)lactate $[[\alpha]_D^{20} - 35.7°$ CHCl$_3$; C=1.55%] was dropwise added at 20° C. The mixture was stirred for 30 minutes. Water was distilled off under reduced pressure, and 45 ml of ethanol was added. Then, while stirring the mixture, 4.8 g of sodium hydroxide was added. The reaction system was flushed with nitrogen, and 4.4 g of hydroquinone dissolved in 25 ml of ethanol was added at 30° C. The mixture was stirred for 2.5 hours. To the reaction product thereby obtained, hydrogen chloride gas was introduced at 30° C. to acidify the reaction system, and then ethanol was distilled off at atmospheric pressure. 20 ml of ethanol and 50 ml of benzene were added, and the solvent was again distilled off under atmospheric pressure. To the residue, 50 ml of water was added, and the mixture was extracted with toluene. The toluene layer was washed with a 5% sodium hydrogen carbonate solution and then with water, and dried, and then toluene was distilled off. The residue was purified by silica gel column chromatography using chloroform, whereby 6.5 g of the desired product ethyl D(+)-2-(4-hydroxyphenoxy) propionate was obtained as a colorless liquid.

$[\alpha]_D^{25} + 43.9°$ CHCl$_3$; C=1.35%, e.e. 96%

EXAMPLE 6

4.4 g of hydroquinone and 67.5 ml of ethanol were charged into a reactor, and after flushing with nitrogen, 6.4 g of sodium hydroxide was added. The mixture was stirred for 1 hour. While cooling the mixture at 10° C., 11.7 g of ethyl L(−)-2-(p-chlorobenzenesulfonyloxy)-lactate $[[\alpha]_D^{20} - 22.5°$ CHCl$_3$; C=1.67%] was dropwise added, and the mixture was stirred for 2 hours. While cooling the reaction product thereby obtained, at 10° C., hydrogen chloride gas was introduced to acidify the reaction system, and the mixture was stirred for 1.5 hours. Then, ethanol was distilled off under reduced pressure. To the residue, 50 ml of water was added, and the mixture was extracted with benzene. The benzene layer was washed with a 5% sodium hydrogen carbonate solution, and then with water, and dried, and then, benzene was distilled off. The residue was purified by silica gel column chromatography using chloroform, whereby 6.0 g of the desired substance ethyl D(+)-2-(4-hydroxyphenoxy) propionate was obtained as a colorless liquid.

$[\alpha]_D^{25}+41.5°$ CHCl$_3$; C=1.27%, e.e. 91%

EXAMPLE 7

4.4 g of hydroquinone and 67.5 ml of ethanol were charged into a reactor, and after flushing with nitrogen, 6.4 g of sodium hydroxide was added. The mixture was stirred for 1 hour. While cooling the mixture at 10° C., 10.3 g of ethyl L(−)-2-(benzenesulfonyloxy)lactate $[[\alpha]_D^{20}-37.9°$ CHCl$_3$; C=1.71%] was dropwise added, and the mixture was stirred for 2 hours. While cooling the reaction product thereby obtained, at 10° C., hydrogen chloride gas was introduced to acidify the reaction system. The mixture was stirred for 2.0 hours. Then, ethanol was distilled off under reduced pressure. To the residue, 50 ml of water was added, and the mixture was extracted with benzene. The benzene layer was washed with a 5% sodium hydrogen carbonate solution, and then with water, and dried, and then benzene was distilled off. The residue was purified by silica gel column chromatography using chloroform, whereby 5.9 g of the desired substance ethyl D(+)-2-(4-hydroxyphenoxy)propionate was obtained as a colorless liquid.

$[\alpha]_D^{25}+37.0°$ CHCl$_3$; C=1.59%, e.e. 81%

EXAMPLE 8

4.4 g of hydroquinone and 67.5 ml of ethanol were charged into a reactor, and after flushing with nitrogen, 6.4 g of sodium hydroxide was added. The mixture was stirred for 1 hour. Then, while maintaining the mixture at 30° C., 7.84 g of ethyl L(−)-2-(methanesulfonyloxy)lactate $[[\alpha]_D^{20}-54.5°$ CHCl$_3$; C=1.76%] was dropwise added, and the mixture was stirred for 1 hour. To the reaction product thereby obtained, hydrogen chloride gas was introduced at 30° C. to acidify the reaction system, and then the mixture was stirred for 1 hour. Then, ethanol was distilled off under reduced pressure. To the residue, 50 ml of water was added, and the mixture was extracted with benzene. The benzene layer was washed with a 5% sodium hydrogen carbonate solution, and then with water, and dried, and then, benzene was distilled off. The residue was purified by silica gel column chromatography using chloroform, whereby 5.9 g of the desired substance ethyl D(+)-2-(4-hydroxyphenoxy) propionate was obtained as a colorless liquid.

$[\alpha]_D^{25}+31.0°$ CHCl$_3$; C=1.55%, e.e. 68%

EXAMPLE 9

1.6 g of sodium hydroxide and 35 ml of water were charged into a reactor. While stirring the mixture, 7.48 g of ethyl L(−)-2-(methanesulfonyloxy)lactate $[[\alpha]_D^{20}-54.5°$ CHCl$_3$; C=1.76%] was dropwise added at 20° C., and the mixture was stirred for 30 minutes. Water was distilled off under reduced pressure, and 45 ml of ethanol was added. Then, while stirring the mixture, 4.8 g of sodium hydroxide was added. After flushing the reaction system with nitrogen, 4.4 g of hydroquinone dissolved in 25 ml of ethanol was added at 30° C., and the mixture was stirred for 2.5 hours. To the reaction product thereby obtained, hydrogen chloride gas was introduced at 10° C. to acidify the reaction system, and then ethanol was distilled off under atmospheric pressure. 20 ml of ethanol and 50 ml of benzene were added, and the solvent was again distilled off under atmospheric pressure. To the residue, 50 ml of water was added, and the mixture was extracted with toluene. The toluene layer was washed with a 5% sodium hydrogen carbonate solution, and then with water, and dried, and then, toluene was distilled off. The residue was purified by silica gel column chromatography using chloroform, whereby 6.0 g of the desired substance ethyl D(+)-2-(4-hydroxyphenoxy)propionate was obtained as a colorless liquid.

$[\alpha]_D^{25}+44.8°$ CHCl$_3$; C=1.57%, e.e. 98%

The boiling point of the compound of the present invention was measured by micro distillation under reduced pressure and found to be from 135° to 137° C./1 mmHg.

EXAMPLE 10

4.4 g of hydroquinone and 67.5 ml of ethanol were charged into a reactor, and after flushing with nitrogen, 6.4 g of sodium hydroxide was added. The mixture was stirred for 1 hour. Then, while maintaining the mixture at 30° C., 10.9 g of ethyl L(−)-2-(benzylsulfonyloxy) lactate $[[\alpha]_D^{20}-18.2°$ CHCl$_3$; C=1.73%] was dropwise added, and the mixture was stirred for 1 hour. To the reaction product thereby obtained, hydrogen chloride gas was introduced at 30° C. to acidify the reaction system, and then the mixture was stirred for 1.5 hours. Then, ethanol was distilled off under reduced pressure. To the residue, 50 ml of water was added, and the mixture was extracted with benzene. The benzene layer was washed with a 5% sodium hydrogen carbonate solution, and then with water, and dried, and then, benzene was distilled off. The residue was purified by silica gel column chromatography using chloroform, whereby 5.8 g of the desired substance ethyl D(+)-2-(4-hydroxyphenoxy) propionate was obtained as a colorless liquid.

$[\alpha]_D^{25}+32.0°$ CHCl$_3$; C=1.39%, e.e. 70%

EXAMPLE 11

0.8 g of sodium hydroxide and 17.5 ml of ethanol were charged to the reactor, and while stirring the mixture, 5.44 g of ethyl L(−)-2-(p-toluenesulfonyloxy)-lactate $[[\alpha]_D^{20}-35.7°$ CHCl$_3$; C=1.55%] was dropwise added at 5° C. The reaction was traced by liquid chromatography (Nucleosyl 5C18; CH$_3$CN/H$_2$O=1), whereby it was found that the ester group was immediately hydrolyzed to form a sodium salt of L(−)-2-(p-toluenesulfonyloxy)lactic acid. The mixture was stirred at 5° C. for 15 minutes, and then hydrogen chloride gas was introduced while maintaining the temperature at 5° C. to acidify the reaction system. Then, the temperature was gradually raised, and ethanol was distilled off under atmospheric pressure. 17.5 ml of ethanol and 50 ml of benzene were added, and the solvent was again distilled off under atmospheric pressure. Then, the mixture was extracted with benzene. The benzene layer was washed with a 5% sodium hydrogen carbonate solution, and then with water, and dried, and then benzene was distilled off. The residue was subjected to distillation under reduced pressure, whereby 5.05 g of ethyl L(−)-2-(p-toluenesulfonyloxy)lactate was recovered. The optical purity was measured, whereby it was found that no substantial racemization took place.

Boiling point: 155°–157° C./0.1 mmHg

Angle of rotation: $[\alpha]_D^{20} -34.0°$ CHCl$_3$; C=1.52%, e.e. 95%

On the other hand, in the case where ethyl L(−)-2-(p-toluenesulfonyloxy)lactate was dropwise added at 50° C., the resulting recovered product had a angle of rotation as low as $[\alpha]_D^{20} -19.5°$ CHCl$_3$; C=1.56%, and an optical purity of e.e. 55%. Then, by using a water solvent instead of the ethanol solvent, ethyl L(−)-2-(p-toluenesulfonyloxy)lactate was hydrolyzed at 10° C., 20° C. or 30° C., respectively, to obtain sodium L(−)-2-(p-toluenesulfonyloxy)lactate. Each reaction solution was subjected to distillation under reduced pressure to remove water, and after an addition of ethanol, subjected to esterification under acidic condition. The recovered ethyl L(−)-2-(p-toluenesulfonyloxy)lactate was not substantially racemized, thus indicating that there was no substantial effect of the temperature in the case where an aqueous solution system was employed.

EXAMPLE 12

4.4 g of hydroquinone and 67.5 ml of ethanol were charged into a reactor, and after flushing with nitrogen, 3.68 g of metallic sodium was added. The mixture was stirred until metallic sodium was completely dissolved. Then, while cooling the mixture at 10° C., 10.9 g of ethyl L(−)-2-(p-toluenesulfonyloxy)lactate $[[\alpha]_D^{20} -35.7°$ CHCl$_3$; C=1.55%] was dropwise added. The mixture was stirred for 1 hour. To the reaction product thereby obtained, acetic acid was added to acidify the reaction system, and then the inorganic substances, etc. were separated by filtration. From the filtrate, ethanol was distilled off under reduced pressure. To the residue, 25 ml of water was added, and the mixture was extracted with benzene. The benzene layer was washed with a 5% sodium hydrogen carbonate solution, and then with water, and dried, and then, benzene was distilled off. The residue was purified by silica gel column chromatography using chloroform, whereby 4.5 g of the desired substance ethyl D(+)-2-(4-hydroxyphenoxy)propionate was obtained as a colorless liquid.

$[\alpha]_D^{25} +2.6°$ CHCl$_3$; C=1.71%, e.e. 4%

EXAMPLE 13

4.4 g of hydroquinone was charged into a reactor, and after flushing with nitrogen, 30 ml of water was added. While stirring the mixture, 3.2 g of sodium hydroxide was added. Hydroquinone was completely dissolved, whereby a uniform solution was obtained. Toluene was added thereto, and water in the system was removed by azeotropic distillation. Then, anhydrous toluene was added, and distilled off under heating. Then, 67.5 ml of anhydrous ethanol was added to obtain a uniform solution, and 10.9 g of ethyl L(−)-2-(p-toluenesulfonyloxy)lactate $[[\alpha]_D^{20} -35.7°$ CHCl$_3$; C=1.55%] was dropwise added at 30° C., and the mixture was stirred for 1 hour. To the reaction product thereby obtained, acetic acid was added to acidify the reaction system. Then, inorganic substances, etc. were separated by filtration, and from the filtrate thereby obtained, ethanol was distilled off under reduced pressure. The residue was dissolved in benzene, and the benzene layer was washed with a 5% sodium hydrogen carbonate solution, and then with water, and dried, and then, benzene was distilled off. The residue was purified by silica gel column chromatography using chloroform, whereby 5.5 g of the desired substance ethyl D(+)-2-(4-hydroxyphenoxy)propionate was obtained as a colorless liquid.

$[\alpha]_D^{25} +9.2°$ CHCl$_3$; C=1.53%, e.e. 20%

REFERENCE EXAMPLE 3.98 g of 2,6-dichloroquinoxaline, 4.2 g of ethyl D(+)-2-(4-hydoxylphenoxy)propionate $[[\alpha]_D^{25} +41.7°$ CHCl$_3$; C=1.35%], 2.76 g of potassium carbonate and 20 g of acetonitrile were mixed. The mixture was refluxed for 6 hours under stirring, and then the solvent was distilled off under reduced pressure. To the residue, 100 ml of toluene and 50 ml of water were added for extraction. The toluene layer was taken, and washed twice with 50 ml of water, and then the solvent was distilled off, whereby 7.4 g of slightly yellow solid was obtained. This solid was purified by silica gel column chromatography using chloroform, whereby 6.5 g of the desired product ethyl D(+)-2-[4-(6-chloro-2-quinoxalinyloxy)phenoxy]propionate was obtained as colorless crystals.

Yield: 87%

$[\alpha]_D^{20} +33.2°$ CHCl$_3$; C=1.20%

The optical purity by the NMR analysis using a shift reagent was 91% e.e.

We claim:

1. A process for preparing a 2-(4-hydroxyphenoxy) alkanoic acid, its ester or alkali metal salt, or an optical isomer thereof, which comprises condensing hydroquinone or an alkali metal salt of hydroquinone with a compound having the formula:

wherein X is a p-toluenesulfonyl group, a methanesulfonyl group, a benzylsulfonyl group, a p-chlorobenzenesulfonyl group or a benzenesulfonyl group, R$^1$ is a hydrogen atom or a lower alkyl group, and R$^2$ is a hydrogen atom, an alkyl group or an alkali metal cation, or its optical isomer in the presence of a base.

2. The process for preparing an alkali metal salt of a 2-(4-hydroxyphenoxy)alkanoic acid according to claim 1, wherein R$^1$ in the formula I is a lower alkyl group.

3. The process according to claim 1, wherein R$^2$ in the formula I is an alkali metal cation, and the condensation is conducted in an inert solvent.

4. The process according to claim 1, wherein R$^2$ in the formula I is a lower alkyl group, and the condensation is conducted in an anhydrous inert solvent.

5. The process according to claim 1, wherein R$^1$ in the formula I is a lower alkyl group, and esterification is conducted with a lower alcohol in the presence of an acid catalyst in the same system.

6. The process according to claim 1, wherein hydroquinone or an alkali metal of hydroquinone is condensed with optically active sodium or potassium 2-(p-toluenesulfonyloxy)lactate to obtain D(+)-2-(4-hydroxyphenoxy)propionic acid, or its ester or alkali metal salt.

7. The process according to claim 1, wherein hydroquinone or an alkali metal of hydroquinone is condensed with optically active sodium or potassium 2-(p-chlorobenzenesulfonyloxy)lactate to obtain D(+)-2-(4-hydroxyphenoxy)propionic acid, or its ester or alkali metal salt.

8. The process according to claim 1, wherein hydroquinone or an alkali metal of hydroquinone is condensed with optically active sodium or potassium 2-

(benzenesulfonyloxy)lactate to obtain D(+)-2-(4-hydroxyphenoxy)propionic acid, or its ester or alkali metal salt.

9. The process according to claim 1, wherein hydroquinone or an alkali metal of hydroquinone is condensed with optically active sodium or potassium 2-(methanesulfonyloxy)lactate to obtain D(+)-2-(4-hydroxyphenoxy)propionic acid, or its ester or alkali metal salt.

10. The process according to claim 1, wherein hydroquinone or an alkali metal of hydroquinone is condensed with optically active sodium or potassium 2-(benzylsulfonyloxy)lactate to obtain D(+)-2-(4-hydroxyphenoxy)propionic acid, or its ester or alkali metal salt.

11. The process according to claim 1, wherein the condensation is conducted with from 0.7 to 2.0 mols of the compound of formula I relative to one mol of hydroquinone or its alkali metal salt.

12. The process according to claim 1, wherein the condensation is conducted at from 20°-70° C. with from 0.7 to 2.0 mols of the compound of formula I relative to one mol of hydroquinone or its alkali metal salt.

* * * * *